United States Patent
Bloch Junior et al.

(10) Patent No.: US 10,588,934 B2
(45) Date of Patent: Mar. 17, 2020

(54) OPIOID PEPTIDE

(71) Applicants: Embrapa—Empresa Brasileira de Pesquisa Agropecuária, Brasília, DF (BR); Fundação Universidade de Brasília (FUB), Brasília DF (BR)

(72) Inventors: Carlos Bloch Junior, Brasília (BR); Mariana Magalhães Nóbrega, Brasília (BR); Karla Graziella Moreira, Catalão (BR); Márcia Renata Mortari, Brasília (BR)

(73) Assignees: EMBRAPA-EMPRESA BRASILEIRA DE PESQUISA AGROPECUARIA, Brasília-DF (BR); FUNDACAO UNIVERSIDADE DE BRASILIA, Brasília-DF (BR)

(*) Notice: Subject to any disclaimer, the term of this patent is extended or adjusted under 35 U.S.C. 154(b) by 0 days.

(21) Appl. No.: 15/504,385

(22) PCT Filed: Aug. 17, 2015

(86) PCT No.: PCT/BR2015/050120
§ 371 (c)(1),
(2) Date: Feb. 16, 2017

(87) PCT Pub. No.: WO2016/026016
PCT Pub. Date: Feb. 25, 2016

(65) Prior Publication Data
US 2017/0232057 A1 Aug. 17, 2017

(30) Foreign Application Priority Data
Aug. 18, 2014 (BR) .............. 102014020348

(51) Int. Cl.
| | |
|---|---|
| A61K 38/08 | (2019.01) |
| C07K 7/06 | (2006.01) |
| A61K 31/485 | (2006.01) |
| A61K 45/06 | (2006.01) |
| A23L 33/10 | (2016.01) |
| A61K 35/66 | (2015.01) |
| A61K 38/00 | (2006.01) |
| A23L 33/18 | (2016.01) |

(52) U.S. Cl.
CPC .............. *A61K 38/08* (2013.01); *A23L 33/10* (2016.08); *A61K 31/485* (2013.01); *A61K 35/66* (2013.01); *A61K 45/06* (2013.01); *C07K 7/06* (2013.01); *A23L 33/18* (2016.08); *A23V 2002/00* (2013.01); *A61K 38/00* (2013.01)

(58) Field of Classification Search
CPC ................................ A61K 38/08; C07K 7/06
See application file for complete search history.

(56) References Cited

U.S. PATENT DOCUMENTS 5,641,861 A * 6/1997 Dooley ................ C07K 5/0812
530/329
5,885,958 A * 3/1999 Zadina ................ C07K 5/1016
435/7.1

OTHER PUBLICATIONS

Li et al. Analgesic properties of chimeric peptide based on morphiceptin and PFRTic-amide. Regulatory Peptides. Nov. 10, 2012, vol. 179, Nos. 1-3, pp. 23-28. (Year: 2012).*
Olsen et al. Hypertension prevalence and diminished blood pressure-related hypoalgesia in individuals reporting chronic pain in a general population: the Tromso study. Pain. Feb. 2013, vol. 154, No. 2, pp. 257-262. (Year: 2013).*

* cited by examiner

*Primary Examiner* — Jeffrey E. Russel
(74) *Attorney, Agent, or Firm* — Sughrue Mion, PLLC

(57) ABSTRACT

The present invention relates to an opioid peptide represented by general formula TyrProPhe-X1-TrpGlyGly-X2-ProPro (SEQ ID NO: 8), wherein:

X1 is represented by Gly or Lys;
X2 is represented by Ile or Val.

The invention also relates to pharmaceutical, nutritional and nutraceutical compositions comprising the peptide and to the use of the same for analgesic purposes, and/or for providing a feeling of satiety, and/or for lowering arterial blood pressure in a subject.

30 Claims, 7 Drawing Sheets

Specification includes a Sequence Listing.

A

B

SEQUENCE LISTING

<160> NUMBER OF SEQ ID NOS: 8

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 1

Tyr Pro Phe Gly Trp Gly Gly Ile Pro Pro
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 2

Tyr Pro Phe Lys Trp Gly Gly Val Pro Pro
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: X is proline, D-lysine or D-ornithine
<220> FEATURE:
<221> NAME/KEY: MISC_FEATURE
<222> LOCATION: (3)..(3)
<223> OTHER INFORMATION: X is tryptophan, phenylalanine, or
      N-alkyl-phenylalanine
<220> FEATURE:
<221> NAME/KEY: MISC_FEATURE
<222> LOCATION: (4)..(4)
<223> OTHER INFORMATION: X is phenylalanine, phenylalanine-NH2, or
      p-Y-phenylalanine, where Y is NO2, F, Cl, or Br

<400> SEQUENCE: 3

Tyr Xaa Xaa Xaa
1

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 4

Tyr Gly Gly Phe Leu
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 5

Tyr Gly Gly Phe Met

```
<210> SEQ ID NO 6
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 6

Tyr Pro Phe Pro
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 7

Tyr Pro Phe Phe
1

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide sequence
<220> FEATURE:
<221> NAME/KEY: MISC_FEATURE
<222> LOCATION: (4)..(4)
<223> OTHER INFORMATION: X is glycine or lysine
<220> FEATURE:
<221> NAME/KEY: MISC_FEATURE
<222> LOCATION: (8)..(8)
<223> OTHER INFORMATION: X is isoleucine or valine

<400> SEQUENCE: 8

Tyr Pro Phe Xaa Trp Gly Gly Xaa Pro Pro
1               5                   10
```

OPIOID PEPTIDE

CROSS REFERENCE TO RELATED APPLICATIONS

This application is a National Stage of International Application No. PCT/BR2015/050120, filed Aug. 17, 2015, claiming priority based on Brazilian Patent Application No. BR102014020348-6, filed Aug. 18, 2014.

FIELD OF THE INVENTION

The present invention relates to opioid peptides and compositions comprising these peptides and it may be applied in the pharmaceutical and food industry.

DESCRIPTION OF THE PRIOR ART

The study of molecules encoded directly by genes has made considerable progress since the last three decades. Thus, the prospection of biologically active peptides has proved to be important both from the biotechnological point of view and from the starting point in several lines of research that include the development of new drugs (Vlieghe et al., 2010) and the production of Genetically modified plants (Brand et al., 2012, Montesinos 2007).

In general, bioactive peptides have been identified as candidates for the development of new drugs, due to some characteristics intrinsic to their biological activity, such as high specificity, potency, low toxicity and chemical and biological diversities (Mason, 2010).

Among the optimization strategies for peptide activity in the body are: i) structural modifications, such as the addition of new molecules, substitution by non-natural amino acid residues and post-translational modifications; and (ii) the drug delivery process, such as encapsulation of peptides in nanostructures (Antosova et al., 2009, Neumann & Staubitz, 2010, Rajendran et al., 2010).

Peptides may exhibit various biological activities, such as antimicrobial (Fjell et al., 2011; Zasloff, 2002), opioid (Goldberg, 2011), hypotensive (Giménez et al., 2011), antithrombotic (Menezes et al., 2011) among others. In 2010, about 60 synthetic peptides with therapeutic potential were already available for pharmaceutical marketing and could be used in multiple pathologies such as allergies, asthma, arthritis, cardiovascular diseases, diabetes, gastrointestinal dysfunction, growth problems, inflammation, obesity, infectious diseases, cancer, osteoporosis, pain, and other vaccines (Stevenson, 2009; Vlieghe et al., 2010).

The sequencing design of new peptides has been used to promote several specific biological activities. Among them, antimicrobial, opioid, hypotensive and antithrombotic activity can be mentioned. Synthetic bioactive peptides with therapeutic potential are employed in multiple pathologies such as allergies, asthma, arthritis, cardiovascular disease, diabetes, gastrointestinal dysfunction, growth problems, inflammation, obesity, infectious diseases, cancer, osteoporosis, pain, vaccines, among others. The production of the bioactive peptides from the processing of longer proteins can be done by endogenous enzymatic processing or even by exogenous processes (Gutstein & Huda, 2006).

With the need to develop novel compounds for treating pain and especially chronic pain, new studies and strategies to enhance the development of drugs have been proposed. Among these studies are those related to peptides.

Opioid peptides are peptides formed from precursor proteins, or pro-hormones, which undergo post-translational modifications leading to the formation of peptides with characteristic biological activities. Studies on opioid activity have contributed to the increase in the number of known peptides belonging to families of opioids and subsequent knowledge of their locations and their roles in modulating the nociceptive process (Millan, 2002). There are three types of classification from the N-terminus of these peptides: i) the terminations of type YGG represent enkephalins and dynorphins, ii) type Yp may be the casomorfinas, morficeptinas, hemorfinas, endorphins, and (iii) Y-D-isomer (Tyr-D-Ala or Tyr-D-Met) reported as deltorfins.

Three different types of opiate receptors are found, namely: mu (β) opioid receptors related to the blocking of stimuli of a thermal nature; the delta (δ) receptors related to mechanical stimulus blockade; and the kappa (κ) receptors in the central nervous system play an activity of antagonism of mu opioid receptors, favoring nociception.

U.S. Pat. Nos. 5,885,958 and 6,303,578 disclose synthesized peptides and their linear and cyclic analogs which bind to the mu opioid receptor. These documents further describe pharmaceutical preparations containing effective amount of such peptides or salts to provide analgesia, relief of gastrointestinal disorders, such as diarrhea, and therapy in the recovery of drug-dependent individuals. The peptides mentioned in U.S. Pat. No. 5,885,958 have the general formula Tyr-X1-X2-X3 (SEQ ID NO: 3), wherein X1 is Pro, D-Lys or D-Orn; X2 is Trp, Phe or N-alkyl-Phe, wherein the alkyl contains from 1 to 6 carbon atoms; and X3 is Phe, Phe-NH2, or p-Y-Phe, where Y is NO2, F, CI or Br.

WO9932510 discloses novel synthetic amino peptides which exhibit high selectivity for kappa opioid receptors and peripheral action, without significant cerebral penetration. According to the respective document, the use of these amino peptides is indicated for the treatment of abdominal pain, bladder disease, inflammatory bowel disease or autoimmune disease and treating other mammals other than humans.

JP55092352 describes the development of a bio-peptide organic compound which can bind to opioid receptors in the brain, with low side effects. U.S. Pat. No. 4,038,222 discloses a peptide isolated from camel pituitaries and their solid phase synthesis procedures, exhibiting opiate agonist activity.

Among the most promising projects for the pharmaceutical industry are those focusing on treatment for cancer, pain and hypertension (Arrowsmith, 2012). Opioid analgesics act on opioid receptors (mu, kappa and delta), G protein-coupled receptors, located mainly in the central nervous system and are considered the most potent class of drugs for the treatment of acute and chronic pain (Stein et al. 2003; Stein & Lang, 2009). They may be prescribed in the treatment of pathologies such as cancer, AIDS, chronic diarrhea and for patients going through heroin detoxification (ibegbu et al., 2011).

Studies on endogenous opioid peptides have made it possible to know about specific amino acid structures that interact with opioid receptors. Enkephalin, morphiceptin and endomorphin-2 are peptides containing the following sequences: YGGFL (SEQ ID NO: 4) (Leu-enkephalin) or YGGFM (SEQ ID NO: 5) (Met-enkephalin), YPFP (SEQ ID NO: 6) and YPFF (SEQ ID NO: 7) respectively. These opioids are present in mammals, located in the CNS, as well as endorphins, dynorphins, endomorphin-1 and bovine beta-casomorphine (Janecka et al., 2010).

Currently, morphine is the main alkaloid isolated from poppy (*Papaver somniferum*), and is used as a drug in the treatment of pain because of its analgesic properties (Law & Loh, 2004).

Due to the main side effects that morphine can cause such as decreased gastrointestinal motility, respiratory depression and tolerance, there is interest in the study of new opioid compounds that can interact with specific targets, producing few adverse effects, low risk for tolerance and higher potency (Goldberg, 2010; Gorzo et al., 2010).

Opioid receptors are involved in the modulation of various physiological mechanisms, which include: antinociception, mood, regulation of the endocrine system and cognitive functions. These receptors are distributed in the central nervous system (CNS) and the human gastrointestinal tract. Some neuropeptides (endogenous opioid peptides acting on the CNS) and beta endorphin are present in the limbic system, which acts to control anxiety and depression. (Barfield, et al. 2013; Holzer, 2009; Vieira & Zarate Jr. 2011).

In addition to the limbic system, some opioid peptides modulate neurotransmission processes in the serotonergic, dopaminergic, noradrenergic pathways that regulate pathophysiologies of depressive disorders. (Fichna, et al. 2007). Among these, serotonin neurotransmission participates in the regulation of stress, mood, and appetite control. The synthesis of serotonin depends on the concentration of its precursor amino acid which is the tryptophan obtained through the ingestion of proteins. The elevation of serotonin levels promotes improvement in mood and decreases the desire to eat. (Peuhkuri et al., 2011).

These neurotransmitter pathways are considered promising therapeutic targets for the treatment of mood-associated disorders and opioid peptides exhibit therapeutic agent potential for the development of new antidepressants. (Fichna, et al. 2007).

Most peptides that are biologically active, i.e. bioactive, are encoded in proteins of animal or plant origin. One way to obtain bioactive peptides is through the ingestion of foods containing protein precursor which undergo proteolysis of digestive enzymes. The main enzymes present in the gastrointestinal tract performing proteolysis in the stomach are pepsin and trypsin and chymotrypsin in the small intestine and other enzymes are also involved in protein cleavage. (Hartmann & Meisel 2007; Korhonen, 2009).

Foods from animal sources that contain bioactive peptides are: milk, dairy, meat and fish. Foods from plant sources are: soy, wheat, among others. A food that stands out in this respect for producing peptides with multiple activities is milk. Hydrolysis of milk protein by digestive enzymes releases bioactive peptides which have opioid, hypotensive, antibacterial activity, among others. These peptides are derived mainly from the proteins casein ($\alpha$ $\beta$ $\kappa$), $\alpha$-lactalbumin, $\beta$-lactoglobulin and glycomacropeptide (GMP). (Hartmann & Meisel 2007; Korhonen, 2009; Meisel, 2005).

Bioactive peptides, besides contributing to the nutritional value of the food, they also exert their physiological effect. In summary, after ingestion of milk proteins, absorption will occur in the gastro intestinal tract, where enzymes will promote the hydrolysis of precursor proteins, releasing the peptides with biological activity. In the case of opioid peptides, they are absorbed into the bloodstream and many can cross the blood brain barrier and cause morphine-like pharmacological responses. The main responses are related to blocking pain stimulus, antinociception, effects on mood control and satiety control (Peuhkuri et al., 2011; Wada & Lonnerdala, 2014).

Several studies have shown that macronutrients used as energy source and present in foods, proteins promote satiety when compared to carbohydrates and fats (Van Kleeff, et al., 2012).

The mechanisms attributed to the satiety of proteins and peptides include: 1—secretion of intestinal hormones, anorexigenics that favor the reduction of food intake, such as CCK (cholecystokinin) and GLP-1 (glucagon-like peptide) or decrease the secretion of orexigenic intestinal hormones that increase food intake, such as ghrelin. 2—increased energy to digest protein compared to carbohydrates and fats 3—high concentration of amino acids in the plasma 4—peptides that are similar to neuropeptides and neurotransmitters that induce satiety via central mechanism. (Foltz et al., 2008; Nishi et al. 2003; Duraffourd, et al., 2012).

In this context, the present invention provides new possibilities for novel sequences of peptides with opioid activity and that have the ability to cross the blood brain barrier having extended action time compared to morphine. Said barrier is rich in enzymes and separates the brain from the systemic circulation preventing the action of drugs in the central nervous system.

In addition, the peptides of the present invention may exhibit dual activity, i.e. opioid activity for pain relief, by blocking antinociception as well as favoring hypotension, due to inhibition of the angiotensin converting enzyme (ACE). This double effect is interesting for the control of chronic pain in hypertensive patients.

SUMMARY OF THE INVENTION

The present invention relates to an opioid peptide or its salt having naloxone-like opioid receptor binding (interaction) activity being represented by the formula:

TyrProPhe-X1-TrpGlyGly-X2-ProPro (SEQ ID NO: 8) wherein:

X1 is represented by Gly or Lys;
X2 is represented by Ile or Val.

The invention further relates to a pharmaceutical composition comprising at least one opioid peptide defined in the invention having similar binding activity to naloxone or its salt and at least one pharmaceutically acceptable carrier.

The invention also relates to a pharmaceutical composition comprising at least one pharmaceutically acceptable excipient and one promoter-forming agent of at least one peptide defined in the invention.

The invention further relates to a food composition comprising at least one food grade substance and at least one peptide defined in the invention.

The invention also relates to a food composition comprising at least one food grade substance and one promoter-forming agent of at least one peptide defined in the invention.

The invention further relates to a nutraceutical composition comprising at least one food grade substance and at least one peptide defined in the invention.

The invention also relates to a nutraceutical composition comprising at least one food grade substance and one promoter-forming agent of at least one peptide defined in the invention.

The invention further relates to the use of the pharmaceutical composition defined therein for providing analgesia in a subject.

The invention also relates to the use of the pharmaceutical composition defined therein for providing a sense of satiety to a subject.

The invention further relates to the use of the pharmaceutical composition defined therein for lowering arterial blood pressure in a subject.

The invention also relates to the use of the food composition defined therein for providing a sense of satiety to a subject.

The invention further relates to the use of the food composition defined therein for lowering arterial blood pressure in a subject.

The invention also relates to the use of the nutraceutical composition defined therein for providing a sense of satiety to a subject.

The invention further relates to the use of the nutraceutical composition defined therein for lowering arterial blood pressure in a subject.

The invention also relates to a method of activating the opioid receptor comprising administering to a subject an effective amount of at least one peptide defined in the invention.

The invention further relates to a method of activating the opioid receptor comprising administering to a subject the pharmaceutical composition defined in the invention.

The invention also relates to a method of activating the opioid receptor comprising administering to a subject the food composition defined in the invention.

The invention further relates to a method of activating the opioid receptor comprising administering to a subject the nutraceutical composition defined in the invention.

The invention also relates to a method of providing analgesia comprising administering to a subject an effective amount of at least one peptide defined in the invention.

The invention further relates to a method of providing analgesia comprising administering to a subject the pharmaceutical composition defined in the invention.

The invention further relates to a method of providing satiety to a subject comprising administering to a subject an effective amount of at least one peptide defined in the invention.

The invention also relates to a method of providing satiety to a subject comprising administering to a subject the pharmaceutical composition defined in the invention.

The invention further relates to a method of providing satiety to a subject comprising administering to a subject the food composition defined in the invention.

The invention further relates to a method of providing satiety to a subject comprising administering to a subject the nutraceutical composition defined in the invention.

The invention also relates to a method of providing lowering of blood pressure of a subject comprising administering to a subject the pharmaceutical composition defined in the invention.

The invention also relates to a method of providing lowering of blood pressure of a subject comprising administering to a subject the pharmaceutical composition defined in the invention.

The invention further relates to a method of providing lowering of blood pressure of a subject comprising administering to a subject the nutraceutical composition defined in the invention.

DETAILED DESCRIPTION OF THE INVENTION

Figure 1:
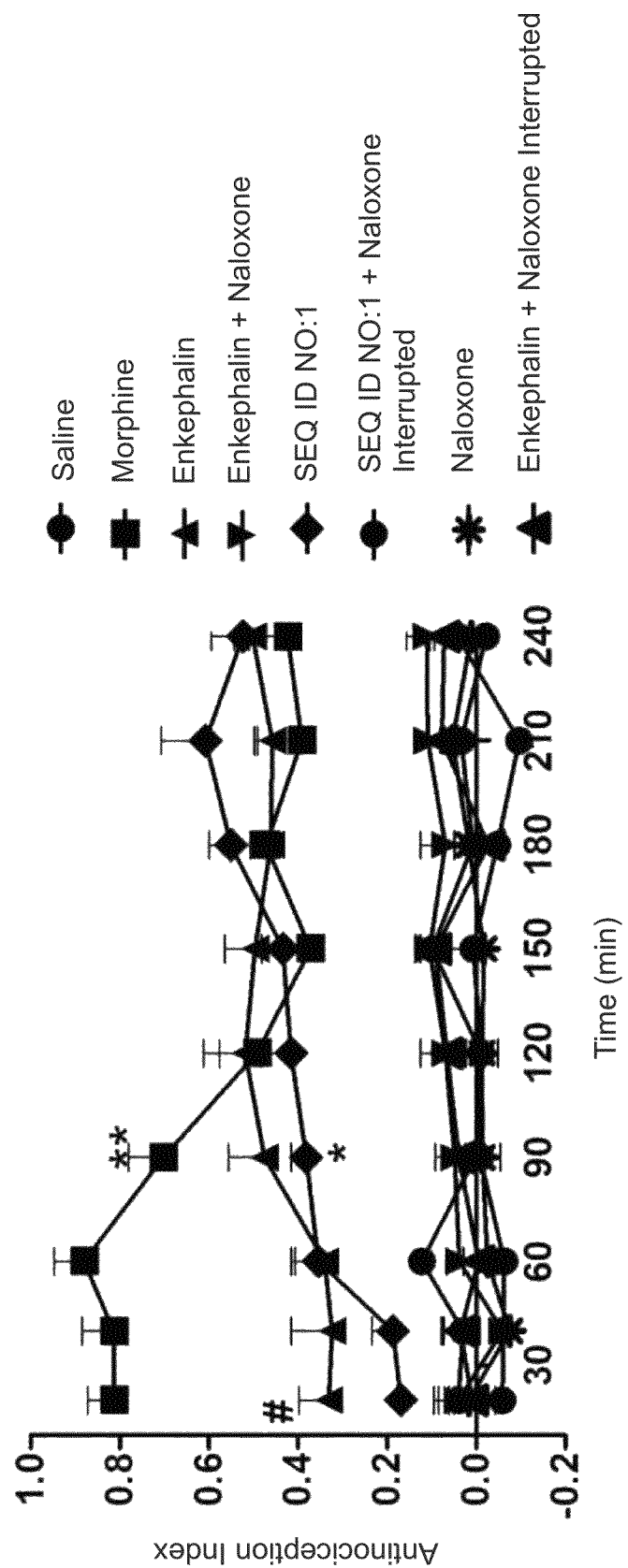
FIG. 1—Index of antinociception, in the tail flick test, represented by symbols (*, **, #) referring to a statistically significant activity (S) and or when significant differences do not occur (NS) when comparing SEQ ID NO:1 to saline, morphine and Leu-enkephalin. In (*) beginning of the activity of SEQ ID NO: 1 $P<0.001$ (S). (**) SEQ ID NO: 1×Morphine with $P>0.05$ (NS). In (*) Leu-enkephalin×SEQ ID NO: 1 $P<0.05$ (NS).
Figure 2:
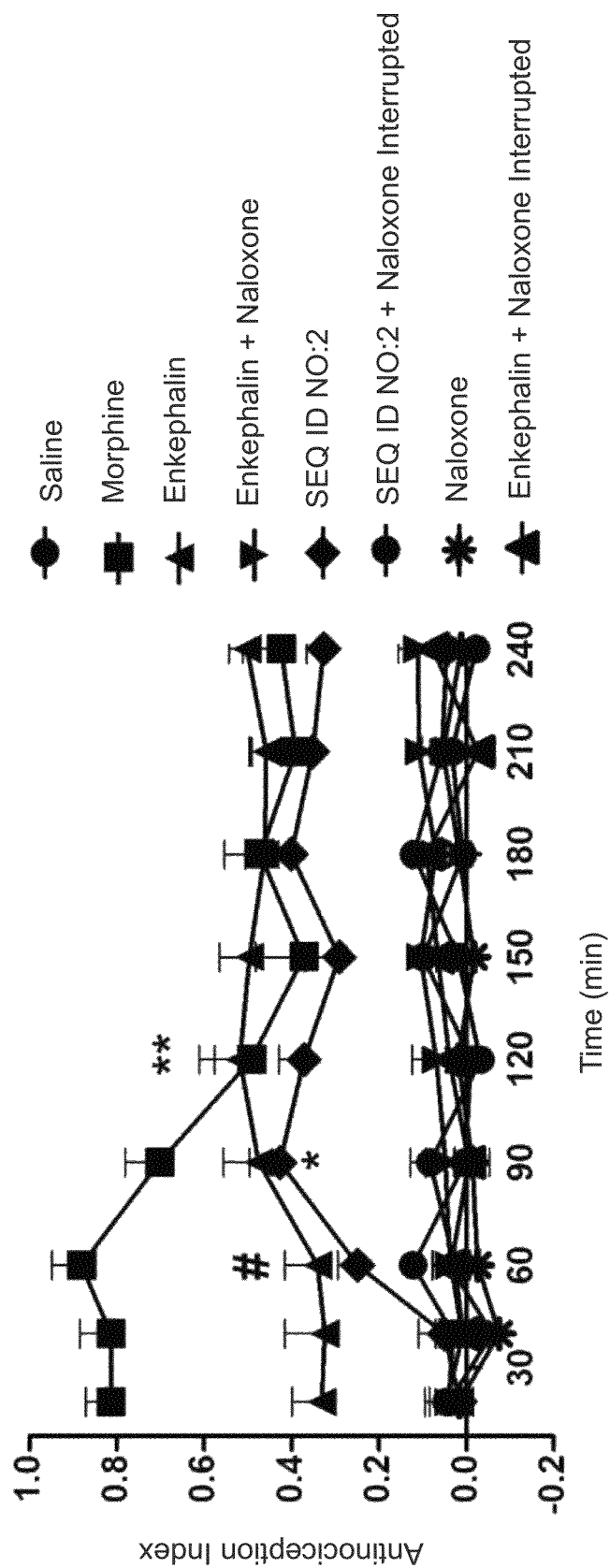
FIG. 2—Index of antinociception, in the tail flick test, referring to SEQ ID NO: 2 when compared to saline, morphine and Leu-enkephalin. In (*) beginning of the activity of SEQ ID NO: 2, $P<0.001$ (S). (**) SEQ ID NO: 2×Morphine with $P>0.005$ (NS). (#) Leu-enkephalin×SEQ ID NO: 2, $P>0.05$ (NS).

The term "patient" used in this invention includes humans and also other mammals such as intensive and extensive breeding animals, zoo animals, companion animals such as cat, dog and horse.

The term "pharmaceutically acceptable carrier" used in the present invention refers to a diluent or adjuvant or excipient or carrier with which or in which the active compound is administered.

The term "therapeutically effective amount" used in the invention refers to the amount of active compound which, when administered to a patient to prevent or treat a condition (such as pain, hunger, etc.) is sufficient to effect such treatment. The therapeutically effective amount varies according to the active compound, the patient's condition, the severity of the condition, the age, weight and other characteristics of the patient.

The term "nutraceutical" used in the invention refers to a food or part of a food that provides medical and health benefits, including prevention and/or treatment of a condition.

The present invention relates to an opioid peptide or salt thereof having naloxone-like binding activity represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the present invention relates to peptides or salts thereof having naloxone-like binding activity and sequences represented by SEQ ID NO: 1 and SEQ ID NO: 2.

The present invention further relates to a pharmaceutical composition comprising at least one opioid peptide or salt thereof having naloxone-like binding activity and at least one pharmaceutically acceptable carrier. The said peptide of the pharmaceutical composition is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the pharmaceutical composition of the present invention are represented by SEQ ID NO: 1 and/or SEQ ID NO: 2.

In the pharmaceutical composition of the invention the concentration of peptide or its salt having naloxone-like binding activity ranges preferably from 0.001% (w/w) to 99.999% (w/w).

In an alternative embodiment of the pharmaceutical composition of the invention, said composition further comprises an analgesic compound. Preferably, said analgesic compound is morphine.

The pharmaceutical composition of the invention may take various pharmaceutical forms. Among them, we can mention: tablet, capsule, elixir, solution, suspension, emulsion, lotion, cream, ointment, granulate, powder or lyophilized powder.

The present invention also relates to a pharmaceutical composition comprising at least one pharmaceutically acceptable carrier and a promoter-forming agent of at least one peptide having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the pharmaceutical composition of the present invention are represented by SEQ ID NO: 1 and/or SEQ ID NO: 2.

In a preferred embodiment of said pharmaceutical composition, the promoter is a genetically modified microorganism.

There are several pharmaceutical forms in which the pharmaceutical compositions of this invention may be present. Among these forms are the tablet, capsule, elixir, solution, suspension, lotion, cream, ointment, granulate, powder or lyophilized powder.

The present invention further relates to a food composition comprising at least one food grade substance and one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the food composition of the present invention are represented by SEQ ID NO: 1 and/or SEQ ID NO: 2.

In the food composition of the present invention the concentration of peptide or its salt having naloxone-like binding activity ranges preferably from 0.001% (w/w) to 99.999% (w/w).

The present invention also relates to a food composition comprising at least one food grade substance and a promoter-forming agent of at least one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the food composition of the present invention are represented by SEQ ID NO: 1 and/or SEQ ID NO: 2. In a preferred embodiment of said food composition of the invention, the promoter-forming agent is a genetically modified microorganism.

The present invention further relates to a nutraceutical composition comprising at least one food grade substance and one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the nutraceutical composition of the present invention are represented by SEQ ID NO: 1 and/or SEQ ID NO: 2.

In the nutraceitucal composition of the present invention the concentration of peptide or its salt having naloxone-like binding activity ranges preferably from 0.001% (w/w) to 99.999% (w/w).

The present invention also relates to a nutraceitucal composition comprising at least one food grade substance and a promoter-forming agent of at least one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the nutraceutical composition of the present invention are represented by SEQ ID NO: 1 and/or SEQ ID NO: 2. In a preferred embodiment of said nutraceitucal composition of the invention, the promoter-forming agent is a genetically modified microorganism.

The present invention further relates to the use of the peptide defined in the invention in order to provide analgesia in an individual. The said peptide is an opioid peptide or salt thereof having naloxone-like binding activity represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the invention relates to the use of at least one peptide selected from those having sequence represented by SEQ ID NO: 1 and SEQ ID NO: 2 for the purpose of providing analgesia in a subject.

The present invention further relates to the use of the peptide defined in the invention in order to provide a sense of satiety to a subject. The said peptide is an opioid peptide or salt thereof having naloxone-like binding activity represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the invention relates to the use of at least one peptide selected from those having sequence represented by SEQ ID NO: 1 and SEQ ID NO: 2 for the purpose of providing a sense of satiety to a subject.

The present invention further relates to the use of the peptide defined in the invention for the purpose of lowering blood pressure of a subject. The said peptide is an opioid peptide or salt thereof having naloxone-like binding activity represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the invention relates to the use of at least one peptide selected from those having sequence represented by SEQ ID NO: 1 and SEQ ID NO: 2 for the purpose of lowering blood pressure of a subject.

The invention further relates to the use of the pharmaceutical compositions described in the invention for providing analgesia in a subject. Said analgesia occurs via the opioid receptor.

The invention further relates to the use of the pharmaceutical compositions described in the invention for lowering arterial blood pressure in a subject.

The invention further relates to the use of the pharmaceutical compositions described in the invention for providing a sense of satiety to a subject. Said sense of satiety occurs via the opioid receptor.

The invention further relates to the use of the food compositions described in the invention for providing a sense of satiety to a subject. Said sense of satiety occurs via the opioid receptor.

The invention further relates to the use of the food compositions described in the invention for lowering arterial blood pressure in a subject.

The invention further relates to the use of the nutraceutical compositions described in the invention for providing a sense of satiety to a subject. Said sense of satiety occurs via the opioid receptor.

The invention further relates to the use of the nutraceutical compositions described in the invention for lowering arterial blood pressure in a subject.

Another object of the invention is a method of activating the opioid receptor, such method comprising administering to a subject an effective amount of at least one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides administered are represented by SEQ ID NO: 1 and/or SEQ ID NO: 2.

Said administration of the opioid peptide of the invention may occur through external, enteral or parenteral application.

It is also an object of the invention a method of activating the opioid receptor, such method comprising administering to a subject a pharmaceutical composition comprising at least one opioid peptide or salt thereof having naloxone-like binding activity and at least one pharmaceutically acceptable carrier. The said peptide of the pharmaceutical composition is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the pharmaceutical composition are represented by SEQ ID NO: 1 and/or SEQ ID NO: 2.

Said administration of the pharmaceutical composition of the invention may be effected through external, enteral or parenteral application.

Another object of the invention is a method of activating the opioid receptor, such method comprising administering to a subject a pharmaceutical composition comprising at least one pharmaceutically acceptable carrier and one promoter-forming agent of at least one peptide having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the pharmaceutical composition are represented by SEQ ID NO: 1 and/or SEQ ID NO: 2. Also preferably, the promoter of the pharmaceutical composition is a genetically modified microorganism.

Said administration of the pharmaceutical composition of the invention may be effected through external, enteral or parenteral application.

Another object of the invention is a method of activating the opioid receptor, such method comprising administering to a subject a food composition comprising at least one food grade substance and an opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the food composition are represented by SEQ ID NO: 1 and/or SEQ ID NO: 2.

Another object of the invention is a method of activating the opioid receptor, such method comprising administering to a subject a food composition comprising at least one food grade substance and a promoter-forming agent of at least one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides are represented by SEQ ID NO: 1 and/or SEQ ID NO: 2. In a preferred embodiment, the peptide promoter-forming agent is a genetically modified microorganism.

Another object of the invention is a method of activating the opioid receptor, such method comprising administering to a subject a nutraceutical composition comprising at least one food grade substance and an opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the nutraceutical composition are represented by SEQ ID NO: 1 and/or SEQ ID NO: 2.

Another object of the invention is a method of activating the opioid receptor, such method comprising administering to a subject a nutraceutical composition comprising at least one food grade substance and a promoter-forming agent of at least one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides are represented by SEQ ID NO: 1 and/or SEQ ID NO: 2. In a preferred embodiment, the peptide promoter-forming agent is a genetically modified microorganism.

Another object of the invention is a method for providing analgesia, such method comprising administering to a subject an effective amount of at least one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides administered are represented by SEQ ID NO: 1 and/or SEQ ID NO: 2.

Said administration of the opioid peptide of the invention may be effected through external, enteral or parenteral application.

It is also an object of the invention a method of providing analgesia, such method comprising administering to a subject a pharmaceutical composition comprising at least one opioid peptide or salt thereof having naloxone-like binding activity and at least one pharmaceutically acceptable carrier. The said peptide of the pharmaceutical composition is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the pharmaceutical composition are represented by SEQ ID NO: 1 and/or SEQ ID NO: 2.

Said administration of the pharmaceutical composition of the invention may be effected through external, enteral or parenteral application.

Another object of the present invention is a method of providing analgesia, such method comprising administering to a subject a pharmaceutical composition comprising at least one pharmaceutically acceptable carrier and one promoter-forming agent of at least one peptide having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the pharmaceutical composition are represented by SEQ ID NO: 1 and/or SEQ ID NO: 2. Also preferably, the promoter of the pharmaceutical composition is a genetically modified microorganism.

Said administration of the pharmaceutical composition of the invention may be effected through external, enteral or parenteral application.

It is also an object of the invention a method of providing satiety to a subject, such method comprising administering to a subject an effective amount of at least one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides administered are represented by SEQ ID NO: 1 and/or SEQ ID NO: 2.

Another object of the invention is a method of providing satiety to a subject, such method comprising administering to a subject a pharmaceutical composition comprising at least one opioid peptide or salt thereof having naloxone-like binding activity and at least one pharmaceutically acceptable carrier. The said peptide of the pharmaceutical composition is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the pharmaceutical composition are represented by SEQ ID NO: 1 and/or SEQ ID NO: 2.

It is also an object of the present invention a method of providing satiety to a subject, such method comprising administering to a subject a pharmaceutical composition comprising at least one pharmaceutically acceptable carrier and one promoter-forming agent of at least one peptide having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the pharmaceutical composition are represented by SEQ ID NO: 1 and/or SEQ ID NO: 2. Also preferably, the promoter of the pharmaceutical composition is a genetically modified microorganism.

Another object of the invention is a method of providing satiety to a subject, such method comprising administering to a subject a food composition comprising at least one food grade substance and an opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the food composition are represented by SEQ ID NO: 1 and/or SEQ ID NO: 2.

Another object of the invention is a method of providing satiety to a subject, such method comprising administering to a subject a food composition comprising at least one food grade substance and a promoter-forming agent of at least one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides are represented by SEQ ID NO: 1 and/or SEQ ID NO: 2. In a preferred embodiment, the peptide promoter-forming agent is a genetically modified microorganism.

Another object of the invention is a method of providing satiety to a subject, such method comprising administering to a subject a nutraceutical composition comprising at least one food grade substance and an opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the nutraceutical composition are represented by SEQ ID NO: 1 and/or SEQ ID NO: 2.

Another object of the invention is a method of providing satiety to a subject, such method comprising administering to a subject a nutraceutical composition comprising at least one food grade substance and a promoter-forming agent of at least one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides are represented by SEQ ID NO: 1 and/or SEQ ID NO: 2. In a preferred embodiment, the peptide promoter-forming agent is a genetically modified microorganism.

It is also an object of the invention a method of providing lowering of arterial blood pressure in a subject, such method comprising administering to a subject an effective amount of at least one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides administered are represented by SEQ ID NO: 1 and/or SEQ ID NO: 2.

Another object of the invention is a method of providing lowering of arterial blood pressure in a subject, such method comprising administering to a subject a pharmaceutical composition comprising at least one opioid peptide or salt thereof having naloxone-like binding activity and at least one pharmaceutically acceptable carrier. The said peptide of the pharmaceutical composition is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the pharmaceutical composition are represented by SEQ ID NO: 1 and/or SEQ ID NO: 2.

It is also an object of the present invention a method of providing lowering of arterial blood pressure in a subject, such method comprising administering to a subject a pharmaceutical composition comprising at least one pharmaceutically acceptable carrier and one promoter-forming agent of at least one peptide having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the pharmaceutical composition are represented by SEQ ID NO: 1 and/or SEQ ID NO: 2. Also preferably, the promoter of the pharmaceutical composition is a genetically modified microorganism.

Another object of the invention is a method of providing lowering of arterial blood pressure in a subject, such method comprising administering to a subject a food composition comprising at least one food grade substance and an opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the food composition are represented by SEQ ID NO: 1 and/or SEQ ID NO: 2.

Another object of the invention is a method of providing lowering of arterial blood pressure in a subject, such method comprising administering to a subject a food composition comprising at least one food grade substance and a promoter-forming agent of at least one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides are represented by SEQ ID NO: 1 and/or SEQ ID NO: 2. In a preferred embodiment, the peptide promoter-forming agent is a genetically modified microorganism.

Another object of the invention is a method of providing lowering of arterial blood pressure in a subject, such method comprising administering to a subject a nutraceutical composition comprising at least one food grade substance and an opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides of the nutraceutical composition are represented by SEQ ID NO: 1 and/or SEQ ID NO: 2.

Another object of the invention is a method of providing lowering of arterial blood pressure in a subject, such method comprising administering to a subject a nutraceutical composition comprising at least one food grade substance and a promoter-forming agent of at least one opioid peptide or salt thereof having naloxone-like binding activity. The said peptide is represented by the sequence:

TyrProPhe-X1-TrpGlyGly-X2-ProPro (SEQ ID NO: 8) wherein:

X1 is represented by Gly or Lys;
X2 is represented by Ile or Val.

Preferably, the peptides are represented by SEQ ID NO: 1 and/or SEQ ID NO: 2. In a preferred embodiment, the peptide promoter-forming agent is a genetically modified microorganism.

Experiments and Results Obtained:

Peptide synthesis: The synthesis of the peptides of the present invention was conducted using the Fmoc/t-butyl (9-fluorenylmethoxycarbonyl) strategy of manual synthesis in solid support (Chan & White, 2000) followed by purification by means of high performance liquid chromatography (HPLC) using a C18 reverse-phase semipreparative column (Vydac).

In vivo analyzes: Tests were carried out on Swiss mice of the *Mus musculus* species, in which nociception tests (hot plate and tail removal test) were used according to Le Bars et al. (2001). Injections were administered via intraperitoneal (IP). Doses were based upon dose and molaridade of the morphine (10 mg/kg animal). As a positive control, Leu-enkephalin (19.3 mg/kg animal) was used in addition to morphine. Sodium chloride saline was used as the negative control and, in order to suspend the antinociceptive effect of Leu-enkephalin and the peptide, serial doses (every hour) of Naloxone (4 mg/kg animal) were injected.

Digestion of the immobilized pepsin precursor: the peptide sequence SEQ ID NO: 2 was digested using immobilized pepsin for a period of 4 hours at 37° C. under agitation of 1400 RPM evaluating the fragmentation index at the times of 15 minutes, 30 minutes, 2 hours and 4 hours.

FIGS. 1,2,3 and 4 represent the raw data obtained from the experiments after statistical analysis. The symbols (*, **, #) indicate the beginning of the statistically significant activity (S) or the statistically non-significant differences (NS). Analyzes of opioid activity were performed in two classical models of studies for this activity: Tail Flick or Hot Plate test.

With the statistical analysis, it was possible to determine at which time (after application) the peptide started to present a statistically significant antinociceptive activity and compare it with the other groups in the tail-flick and hot plate tests.

In the tail-flick test, shown in FIG. 1, the peptide SEQ ID NO: 1 started its statistically significant action after 90 min. (*) up to 240 min. with P<0.001, in relation to the saline solution, negative control group. Comparing with morphine, positive control, SEQ ID NO: 1 showed no significant difference after 90 min. (**) with values of P>0.05. In the case of Leu-enkephalin, peptide positive control, there was no significant difference throughout the assay, i.e., SEQ ID NO: 1 showed a profile similar to that of Leukephalin (#) with P>0.05.

Except for the time of 30 min, there were significant differences between SEQ ID NO: 1 and SEQ ID NO: 1+naloxone during the 4 hour analysis, with P values<0.001.

As expected, there were no significant differences in activity profile between the following groups: saline, naloxone, SEQ ID NO: 1+naloxone and Leu-enkephalin+naloxone.

Analyzing the results for the peptide of SEQ ID NO: 2 (FIG. 2), its activity started at 90 minutes and lasted until the end of the test, except for the time of 150 minutes, when no significant difference was found in relation to the saline P<0.05. Regarding morphine, from the time of 120 minutes, there were no significant differences (P>0.005) with SEQ ID NO: 2 until the end of the test at 240 minutes. When compared to Leu-enkephalin, from the time of 60 minutes, SEQ ID NO: 2 did not show significant differences (#) with P>0.05.

At the other times (before 60 minutes) the difference was statistically significant with P<0.01. From 60 minutes there was a significant difference in the activity profile of SEQ ID NO: 2 when compared to SEQ ID NO: 2+naloxone with P<0.001 and it was maintained up to 240 minutes.

There were no significant differences in activity profile between the following groups: saline, naloxone, SEQ ID NO: 2+naloxone and Leu-enkephalin+naloxone.

Figure 3:
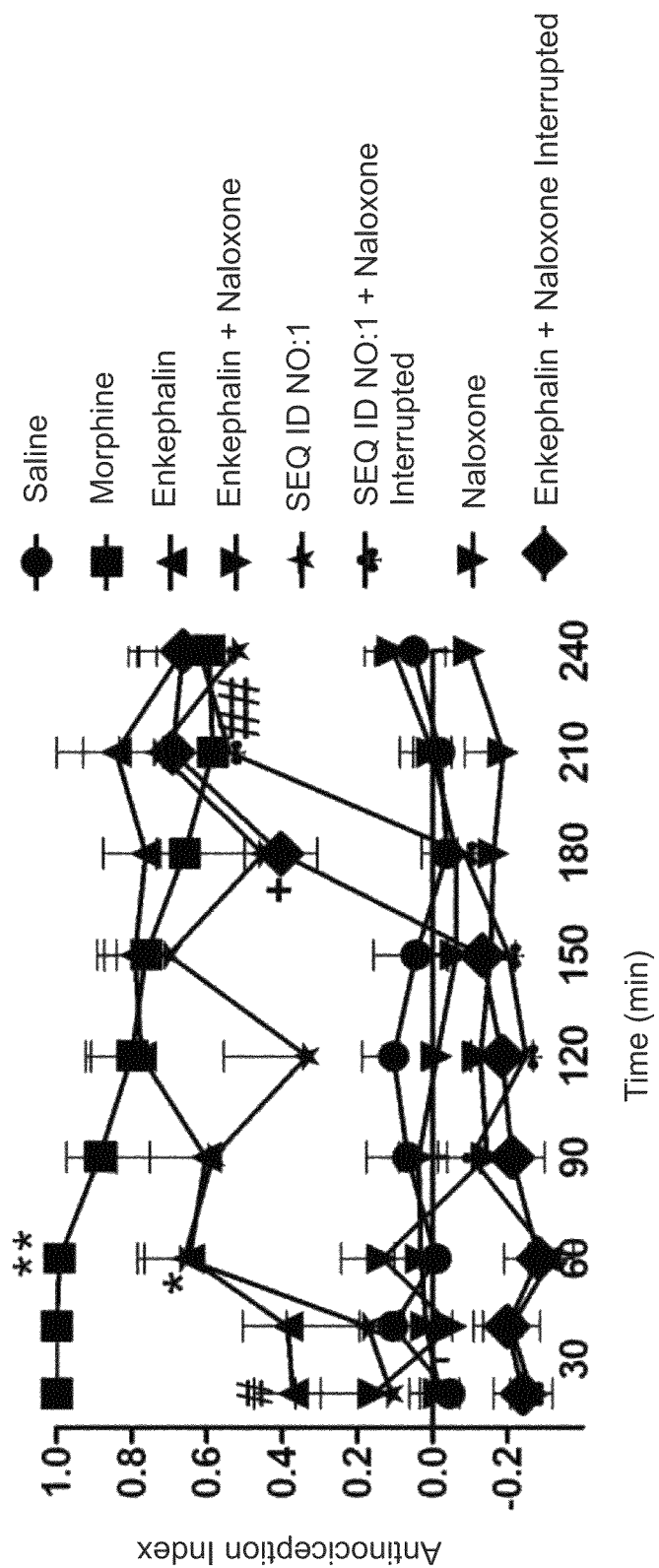
FIG. 3—Index of antinociception, in the hot plate, referring to SEQ ID NO: 1 when compared to saline, morphine and Leu-enkephalin. In (*) beginning of the activity of, $P<0.01$ (S). (**) SEQ ID NO: 1× Morphine with $P>0.05$ (NS). (#) Leu-enkephalin×SEQ ID NO: 1, $P>0.05$ (NS). (##) SEQ ID NO:1×SEQ ID NO:1+naloxone $P>0.05$ (NS).
Figure 4:
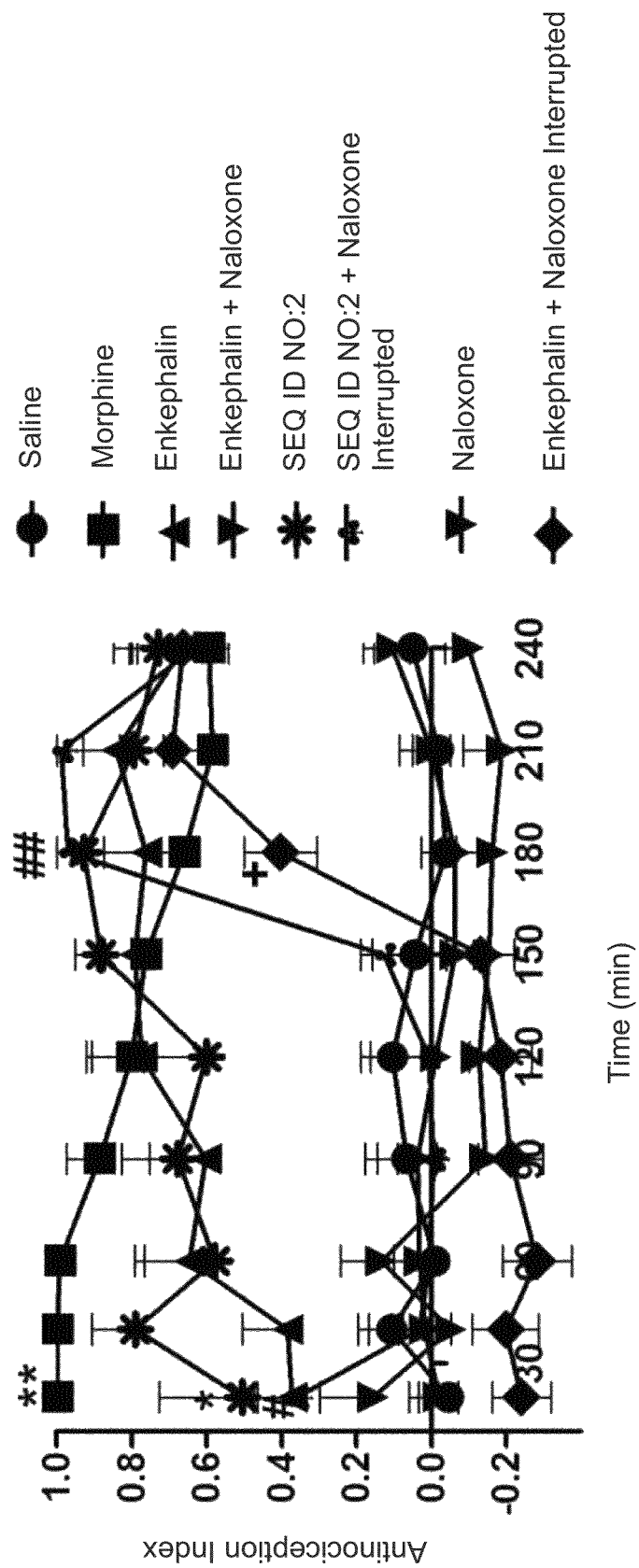
FIG. 4—Index of antinociception, in the hot plate, referring to SEQ ID NO: 2 when compared to saline, morphine and Leu-enkephalin. In (*) beginning of the activity of SEQ ID NO: 2, $P<0.001$ (S). (**) SEQ ID NO: 2× Morphine with $P>0.005$ (NS). (#) Leu-enkephalin×SEQ ID NO: 2, $P>0.05$ (NS). (##) SEQ ID NO:2×SEQ ID NO:2+naloxone $P>0.05$ (NS).

In the Hot Plate test shown in FIG. 3, SEQ ID NO: 1 started its activity at 60 minutes, as it presented statistically significant differences in relation to saline with P<0.01 (*). It is noteworthy that at the time of 120 minutes, there was no significant difference, P>0.05.

Comparing the activity profile of the SEQ D NO: 1 with morphine, at the time of 30 minutes, there was a significant difference with P<0.001. From 60 minutes there were no statistically significant differences up to 240 minutes (**) with P>0.05. There were also no statistically significant differences between the SEQ ID NO: 1 and the Leu-enkephalin (#) with P>0.05, this value being constant throughout the test. In the assays with SEQ ID NO: 1+naloxone when compared to SEQ ID NO: 1, there were no significant differences only at 210 minutes and 240 minutes (##) P>0.05 which are the times at which the peptide returned to action after administration of naloxone was discontinued. With the discontinuation of naloxone administration in the naloxone+Leu enkephalin group, it can be observed that Leu-enkephalin activity has also been resumed.

There were no significant differences in activity profile between the following groups (which was expected): saline, naloxone, SEQ ID NO: 2+naloxone and Leu-enkephalin+naloxone.

Since the beginning of the test, the peptide SEQ ID NO: 2 (FIG. 4) started acting. There were statistically significant differences in relation to saline (*) with P<0.001 which persisted throughout the test. SEQ ID NO: 2 when compared to morphine (**) and Leu-enkephalin (#) did not show statistically significant differences, with P>0.05 during the entire assay.

At 180 minutes to 240 minutes there were no statistically significant differences between SEQ ID NO: 2+naloxone and SEQ ID NO: 2, (##) with P>0.05. The other times showed significant differences with P<0.001.

There were no significant differences in activity profile between the following groups: saline, naloxone, SEQ ID NO: 2+naloxone and Leu-enkephalin+naloxone.

Figure 5:
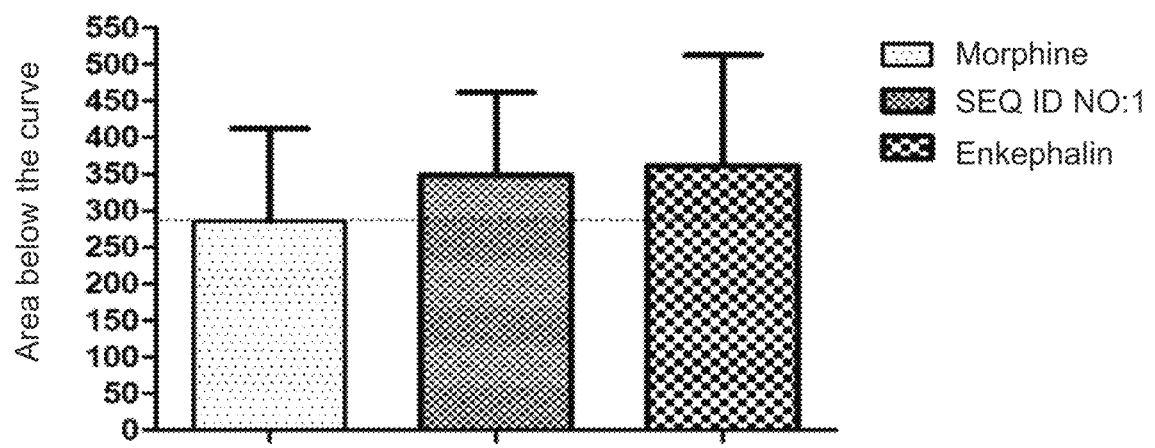
FIG. 5—A. Determining the area below the curve in the tail flick test, for SEQ ID NO: 1; B. Determining the area below the curve in the tail flick test, for SEQ ID NO: 2
Figure 5:
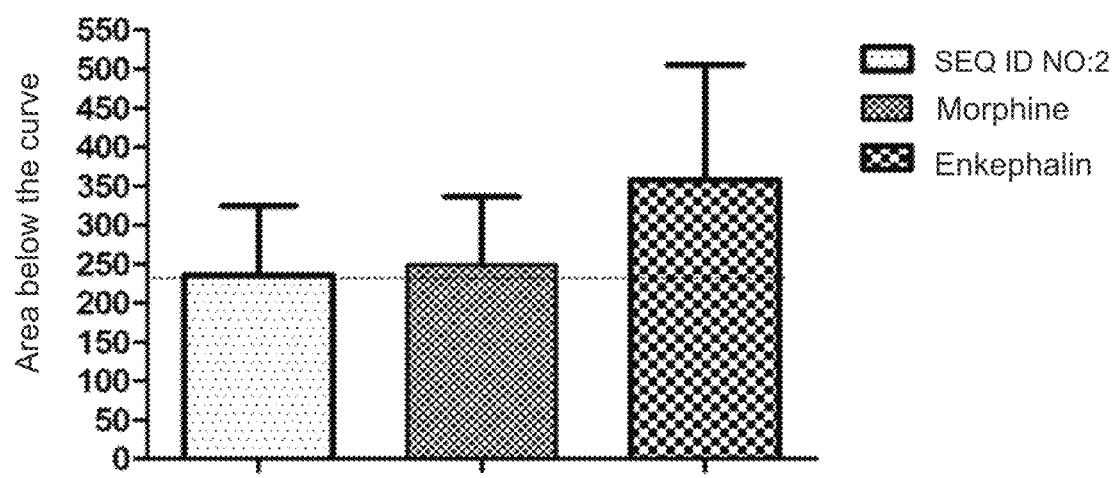

Besides the analysis of variance, the area under the curve was also determined for each experimental group and positive controls (morphine and enkephalin). This analysis aimed at obtaining values for the cumulative effect acquired during the test. FIG. 5A shows that SEQ ID NO: 1, in the tail flick test, showed a cumulative effect over time greater than morphine and similar to Leu-enkephalin, which showed no statistically significant differences over the test with p>0.05 (NS).

In relation to the area below the curve, it can be noted that SEQ ID NO: 2 in the tail flick test showed lower cumulative effect to morphine and Leu-enkephalin (FIG. 5B).

Figure 6:
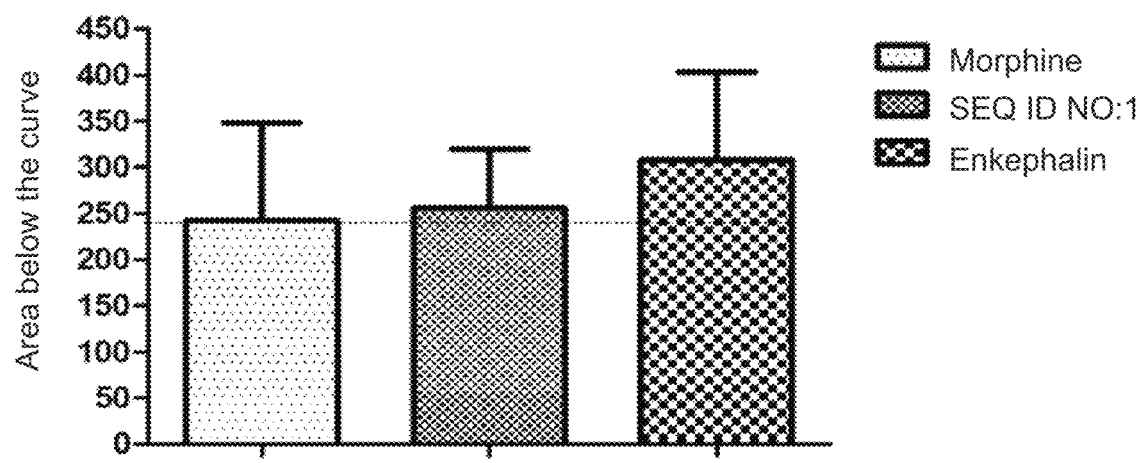
FIG. 6—A. Determining the area below the curve, in the hot plate test, for SEQ ID NO: 1; B. Determining the area below the curve, in the hot plate test, for SEQ ID NO: 2; B.
Figure 6:
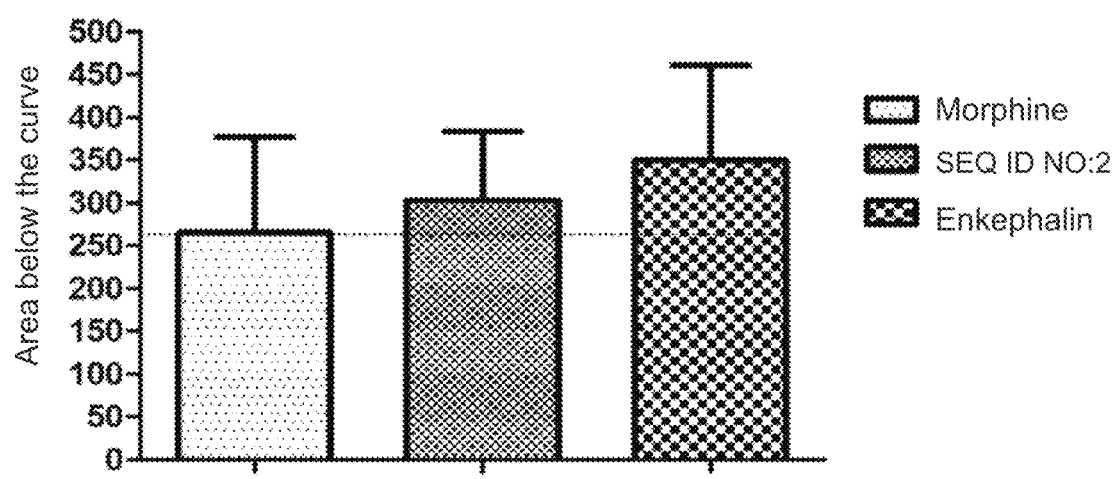

The area below the curve on the hot plate, demonstrates that SEQ ID NO: 1 (FIG. 6A) exhibited a higher cumulative effect similar to morphine and Leu-encefaiina, because there was no significant difference (SEQ ID NO: 1×Leu-enkephalin) with P value>0.05 (NS) throughout the test.

The cumulative effect of SEQ ID No: 2 in the hot plate test (FIG. 6B) also showed indices area below the curve most similar to morphine and Leu-encefaiina (P>0.05).

Figure 7:
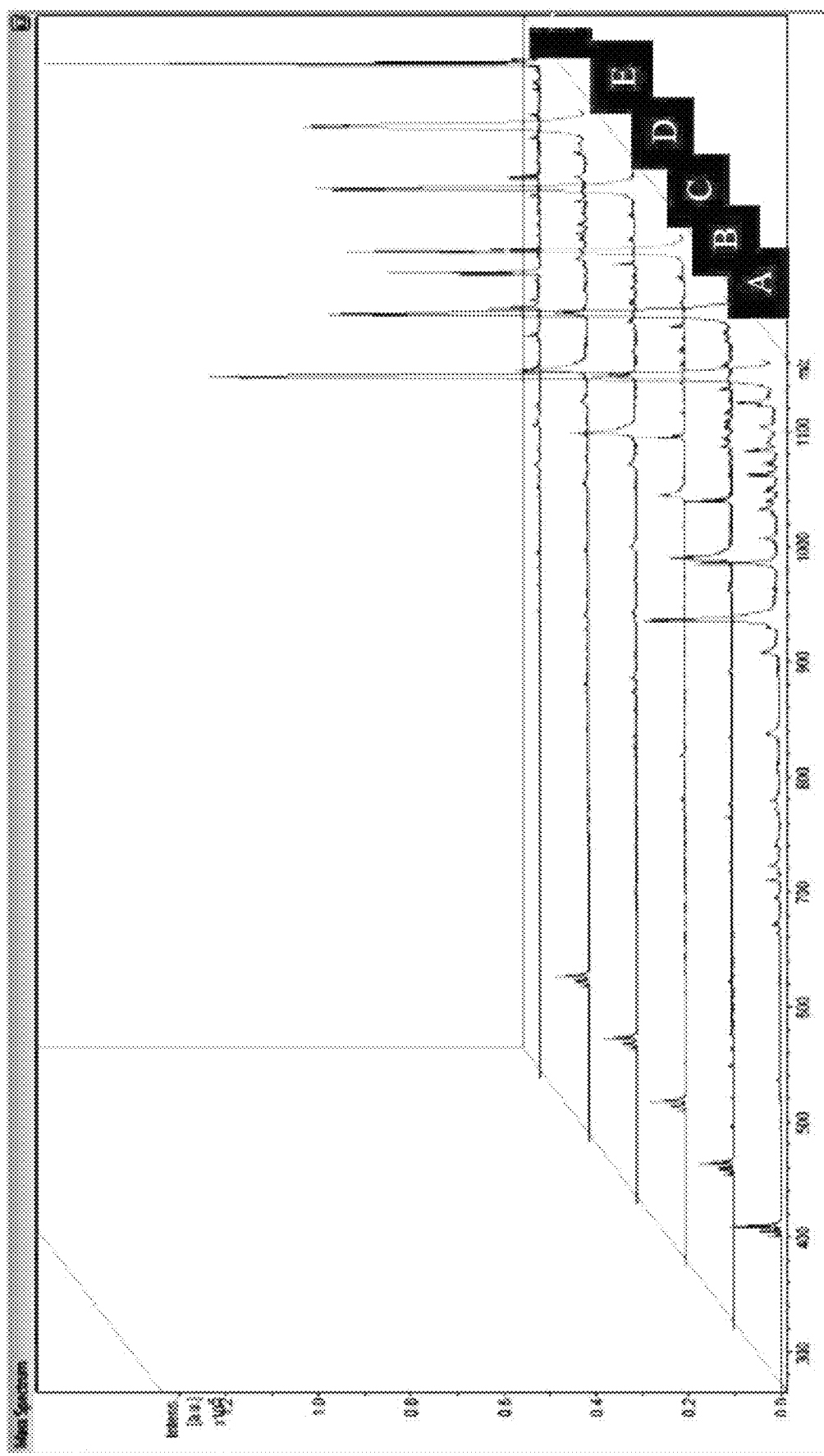
FIG. 7. Representation of the fragments obtained at the different incubation times with the enzyme trypsin. Analysis performed by mass spectrometry, MALDI. The first spectrum, marked with the letter A, refers to the time of 15 minutes; The second spectrum marked with the letter B indicates the time of 30 minutes; C indicates the time of 1 hour; D indicates the time of 2 hours; E indicates the time of 4 hours and, finally, F is the control peptide (SEQ ID NO: 2).

Digestion of the precursor ion referring to SEQ ID NO: 2 (FIG. 7) shows that during incubation with trypsin enzyme (enzymes present in the gastrointestinal tract) the major peak of SEQ ID NO: 2 will reduce its intensity. Through this experiment it was possible to try to observe in vitro the digestion of the peptide.

The invention claimed is:

1. Opioid peptide or salt thereof having naloxone-like binding activity characterized in that it is represented by formula:

TyrProPhe-X1-TrpGlyGly-X2-ProPro (SEQ ID NO: 8) wherein:

X1 is represented by Gly or Lys;
X2 is represented by Ile or Val.

2. A peptide according to claim 1 characterized by being SEQ ID NO: 1.

3. A peptide according to claim 1 characterized by being SEQ ID NO: 2.

4. A pharmaceutical composition characterized by comprising at least one opioid peptide having naloxone-like binding activity defined in claim 1 or salt thereof and at least one pharmaceutically acceptable carrier.

5. A pharmaceutical composition according to claim 4, characterized by having a concentration of peptide or salt thereof in the composition ranging from 0.001% (w/w) 99.999% (w/w).

6. A pharmaceutical composition according to claim 4 characterized by comprising an analgesic compound.

7. A pharmaceutical composition according to claim 6 characterized by comprising morphine as the analgesic compound.

8. A pharmaceutical composition according to claim 4 characterized in that it is in the pharmaceutical form selected from a tablet, capsule, elixir, solution, suspension, emulsion, lotion, cream, ointment, granulate or powder.

9. A pharmaceutical composition comprising at least one pharmaceutically acceptable carrier, and further comprising a genetically-modified microorganism that expresses the peptide according to claim 1.

10. The pharmaceutical composition according to claim 9, wherein said composition is in a pharmaceutical form selected from the group consisting of a tablet, a capsule, an elixir, a solution, a suspension, a lotion, a cream, an ointment, a granulate or a powder.

11. A food composition characterized in that it comprises at least one food grade substance and at least one peptide defined in claim 1.

12. A food composition according to claim 11 characterized in that it comprises an amount of peptide or salt thereof ranging from 0.001% (w/w) to 99.999% (w/w).

13. A food composition comprising at least one food-grade substance, and further comprising a genetically-modified microorganism that expresses the peptide according to claim 1.

14. A nutraceutical composition characterized in that it comprises at least one food grade substance and at least one peptide defined in claim 1.

15. A nutraceutical composition according to claim 14 characterized in that it comprises an amount of peptide or salt thereof ranging from 0.001% (w/w) to 99.999% (w/w).

16. A nutraceutical composition comprising at least one food-grade substance, and further comprising a genetically-modified microorganism that expresses the peptide according to claim 1.

17. A method of activating an opioid receptor characterized in that it comprises administering to a subject an effective amount of at least one peptide defined in claim 1.

18. A method of activating an opioid receptor characterized in that it comprises administering to a subject a pharmaceutical composition as defined in claim 4.

19. A method of activating an opioid receptor characterized in that it comprises administering to a subject a food composition as defined in claim 11.

20. A method of activating an opioid receptor characterized in that it comprises administering to a subject a nutraceutical composition as defined in claim 14.

21. A method of providing analgesia characterized in that it comprises administering to a subject an effective amount of at least one peptide defined in claim 1.

22. A method of providing analgesia characterized in that it comprises administering to a subject a pharmaceutical composition as defined in claim 4.

23. A method of providing satiety to a subject characterized in that it comprises administering to a subject an effective amount of at least one peptide defined in claim 1.

24. A method of providing satiety to a subject characterized in that it comprises administering to a subject a pharmaceutical composition as defined in claim 4.

25. A method of providing satiety to a subject characterized in that it comprises administering to a subject a food composition as defined in claim 11.

26. A method of providing satiety to a subject characterized in that it comprises administering to a subject a nutraceutical composition as defined in claim 14.

27. A method of lowering blood pressure characterized in that it comprises administering to a subject an effective amount of at least one peptide defined in claim 1.

28. A method of lowering blood pressure characterized in that it comprises administering to a subject a pharmaceutical composition as defined in claim 4.

29. A method of lowering blood pressure characterized in that it comprises administering to a subject a food composition as defined in claim 11.

30. A method of lowering blood pressure characterized in that it comprises administering to a subject a nutraceutical composition as defined in claim 14.

* * * * *